US00PP15899P2

(12) United States Plant Patent
White

(10) Patent No.: US PP15,899 P2
(45) Date of Patent: Jul. 26, 2005

(54) MINIATURE ROSE PLANT NAMED 'SAVASALUTE'

(50) Latin Name: *Rosa hybrida*
Varietal Denomination: SAVasalute

(75) Inventor: Wendy R. White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 11 days.

(21) Appl. No.: 10/857,794

(22) Filed: May 28, 2004

(51) Int. Cl.[7] ..... A01H 5/00
(52) U.S. Cl. ..... Plt./122
(58) Field of Search ..... Plt./122

*Primary Examiner*—Anne Marie Grunberg
*Assistant Examiner*—Annette H Para

(57) ABSTRACT

'SAVasalute' is a new and distinct variety of miniature rose plant primarily identified by its dark red, non fading flowers of exhibition, hybrid tea form on straight stems held above the plant making them ideal for cutting. Fragrance is so slight as to be of no significance. Its dark green, semi-glossy foliage has shown very good disease resistance in national, outside testing. 'SAVasalute' is hardy at least to zone 4 and heat tolerant at least to zone 9.

1 Drawing Sheet

Genus and species: *Rosa hybrida 'minima'*.
Varietal denomination: 'SAVasalute'.

CROSS REFERENCE

There are several miniature rose varieties of this same breeding program which bear some resemblance to this new invention by color and flower size, however the new invention bears considerable resemblance to 'BENblack' (Black Jade, U.S. Plant Pat. No. 5,925), from the related breeding program of Frank Benardella. Frank Benardella was in constant communication with the originator of this breeding program, Harmon Saville, regarding hybridizing. The two programs often used some of the same plants to create their own individual breeding lines.

Similarities: Both 'BENblack' and this new invention have dark red flowers with little fade as the bloom ages; both have hybrid tea formed flowers, measuring 1½ inches across when expanded to optimal exhibition stage and similar petal count; both plants mature at about the same height, with an upright habit and carrying their blooms on straight stems above the plant.

Differences: The most noticeable differences between 'BENblack' and this new invention are in the overall appearance of the plants. The leaflets and overall size of the foliage are smaller on this new invention as well as having a more compact plant habit. New stems of this new invention mostly originate from the roots, below the ground surface, while 'BENblack' primarily has a main stalk that additional stems originate from. In full sun, the flowers of 'BENblack' become near black from additional anthocyanin coloration while the flowers of this new invention remain a deep red.

The lineage of both these plants can be traced back to 'Sheri Ann' (U.S. Plant Pat. No. 3,826, expired). 'Sheri Ann' is the seed parent of 'BENblack'. It is also in both the second and third generations of this new invention on both the seed parent and pollen parent sides.

RIGHTS TO THE INVENTION

Be it known that I, Wendy R. White of Ipswich, Mass., claim invention of new and useful improvements in ROSE PLANT/var. 'SAVasalute' and following is a clear and exact description of the same.

BACKGROUND OF THE INVENTION

This present invention relates to a new and distinct variety of hardy, bush type plant of the miniature rose class. This new variety was created by me under controlled conditions in a greenhouse in Rowley, Mass. by crossing the following two rose plants:

The seed parent is an unintroduced, miniflora seedling of 'Party Girl' (U.S. Plant Pat. No. 4,598, expired) by 'SAVabear' (U.S. Plant Pat. No. 7,424).

The pollen parent is also an unintroduced seedling of 'SAValav' (U.S. Plant Pat. No. 9,031) by 'Party Girl'.

The idyllic goals of this breeding program are to produce unique miniature roses with the two qualities of disease resistance and fragrance, along with hardiness and exhibition, hybrid tea form blooms in abundance from late spring to late fall. Roses chosen as pollen and seed parents for this program are chosen for having 2 or, when feasible, more of the qualities of hybrid tea, exhibition form; disease resistance; hardiness; fragrance. These roses are crossed with miniature roses having, primarily, abundant bloom production and, preferably, any other of the additional desired qualities.

The seed parent is a miniflora tested hardy to zone 5 and with excellent hybrid tea form and slight fragrance. The pollen parent was a miniature with good, hybrid tea form, was very fragrant and showed exceptional disease resistance. Although crossing these two roses did not yield significant fragrance, the new invention has exhibition, hybrid tea form, has tested hardy to zone 4 and has very good, overall, disease resistance.

This present invention bares resemblance to its parents. Traits from its seed parent are excellent hybrid tea form flowers on long, straight stems, held above the plant and usually borne one to a stem. Traits from the pollen parent are the miniature plant habit and exceptional disease resistance.

Differences from its parents are visually obvious. The seed parent is a larger, red and white blend miniflora with a more open plant habit, while this new invention is a more compact, miniature rose plant with non-fading deep red flowers. The pollen parent has deep mauve, near purple flowers on short stems and a low growing, somewhat open plant habit. The new invention is half again taller then the pollen parent, more compact and with smaller and dark red flowers borne on long cutting stems.

Asexual reproduction by cuttings of this new variety in Rowley, Mass. and Arroyo Grande, Calif. shows that all distinguishing characteristics of this rose continually come true to form.

SUMMARY OF THE INVENTION

The present invention relates to a new and distinct variety of hardy dwarf bush type rose plant of the miniature class. The characteristics distinguishing it from its parents and from all other varieties of which I am aware are its unique combination of flower color, form, size and petal count combined with its plant habit and degree of resistance. More specifically, those distinguishing characteristics are dark red, non fading flowers of exhibition, hybrid tea form, having 15 to 20 petals and an open bloom size of 1½ inches, on straight stems held above a plant growing upright to 16 to 22 inches with good disease and insect resistance.

The variety is further characterized by:

An abundance of these flowers borne mostly singly from late spring to mid-autumn on long stems making them ideal for cutting Long lasting cut flowers for arranging or exhibition 4 rows of petals opening slowly to expose bright yellow stamens A plant with dark green, semi-glossy foliage Exceptional hardiness in national, outside testing for both heat and cold Fragrance so slight as to be of no significance A plant that grows and blooms both in the greenhouse and outdoors, providing decoration in the garden as a specimen plant or a low hedge, or in large containers.

BRIEF DESCRIPTION OF THE DRAWING

The accompanying color photograph, taken in April, shows specimens of the flower of this new variety of the buds and flowers in different stages of development, from bud to open blooms with sepals and young and older foliage and stems as grown under plastic in San Luis Obispo County, Calif.

BOTANICAL DESCRIPTION OF THE PLANT

The following observations, measurements, values and comparisons describe 4 and 5 years old plants of *rosa hybrida* minima, 'SAVasalute', of the miniature rose class, grown in 2-gallon, plastic nursery containers in plastic covered houses in Essex County, Mass. The detailed description is presented here in outline form. Color references are made using The Royal Horticultural Society (London, England) Colour Chart, except where common terms of color are used.

FLOWERS

Blooming habit: Continuous.

Borne: Mostly singly and occasionally with sprays of three. The first flush of bloom in the spring has a larger quantity of its blooms borne in sprays. The remainder of the year the majority of flowers are borne singly.

Bud: Size: ¾ of an inch in length and ½ inch diameter at the widest point just before the sepals divide.

*Form.*—Ovate with an acute tip Color when sepals first divide — near 53A.

Sepals: Color — outer surface near 138A inside surface near 183B.

*Size.*—3 innermost sepals are ⅝ inch long, 1 outer is ⅝ inch long and 1 outer is ⅞ inch long and all are ¼ inch wide, excluding any foliar appendages.

*Form.*—Elongated oval, acuminate apices extending beyond the tip of the bud, with a truncate base.

*Characteristics.*—2 outermost sepals have 1 or 2 lanceolate, foliar appendages on each margin and usually lanceolate apices instead of or appended to the acuminate apex with 0 to 6 smaller foliar appendages along their margins; margins of the 2 innermost sepals are entire; one sepal in-between has one margin as those of the inner sepals and one margin as those of the outermost sepals; rolling back just ahead of the petals, remaining near perpendicular to the receptacle until the petals begin to drop and then rolling back to a 45 degree angle with the peduncle, remaining permanently attached to the receptacle and dropping together with the peduncle.

*Surface texture.*—Inside surface is pubescent, outer surface has a few, very fine, single hairs.

Peduncle size: 1¼ inches long, 7/64 inch diameter.

*Aspect.*—Straight.

*Strength.*—Strong.

*Color.*—Anthocyanin coloration is present, near 146C flushed with near 183B on any area exposed to full sun.

*Texture.*—Smooth.

*Surface.*—A modicum of very fine hairs.

Receptacle: Size — 4/16 to 5/16 inch diameter and 3/16 inch high.

*Color.*—Near 144A with one side flushed with near 183A or sometimes entirely flushed with near 177C.

*Texture.*—A few, single fine hairs, randomly spaced.

*Top of receptacle.*—Shape, round. Color — a very light yellow-green, near 1D. Size — about — ⅜ inch diameter. Surface — matte, glabrous, an alveola in the center that is villous and out of which the styles originate.

Bloom: Size: When fully expanded averages 1½ to 1¾ inches across, average 1 inch high, measured from the receptacle.

*Form.*—The upper profile is flat as soon as the petals start to unfurl and remains flat until the petals drop. The lower profile goes from cupped when the petals start to unfurl to slightly convex when the flower is fully open.

*Lasting quality as cut flower.*—5 to 8 days.

*Fragrance.*—Slight.

*Petalage.*—Under normal conditions 15 to 20.

*Petaloids.*—None to 4.

*Petals.*—Texture: glabrous, medium thickness.

*Appearance.*—Inside — velvety, outside — satiny.

*Surface.*—Upper surface, puberken, giving the velvety appearance, and has several single hairs, occasionally more in the vicinity of the primary vein near the base of the petal but not near the point of attachment under surface has a very few randomly placed, single hairs.

*Form.*—Broad, ovate-rotundate; outer edge, rounded; base is obtuse.

*Margin.*—Entire with a cuspidate apex except occasionally any marking being absent on some of the outer most petals; under ×10 microscope it can be noted the margin is actually sinuate.

*Length and width of outer petals.*—As wide as long, ¾ to ⅞ inch.

*Arrangement.*—Imbricated.

*Persistence.*—Drop off cleanly in 10 to 14 days.

*Color.*—During the first few days — inner and outer petals near 53A, near 16C at the point of attachment which lightens to near 11D ⅛ of the way up and into the petal at which point the color is a lighter red, near 184C from the greyed-purple group, upwards for an equal distance before blending into the 53A for the remaining ¾ of the petal. (Occasionally 1 or more of the outermost petals will have a white streak, near 155D, from the point of attachment, starting out from the petal base as from 1/16 inch to ⅛ inch wide, going up and sometimes digressing out into the petals in random branching patterns. This streak is satiny in texture, not having the puberkin covering. Occasionally the dark red suffuses in varying amounts with the white giving pink coloring, near 55A, 55B or 55C.) Reverse of both inner and outer petals — near 53A and becoming near 53B toward the base and white, near 158C, at the points of attachment (Any white streaking from the inner surfaces does not show on the reverse of the petals) Color as the bloom ages — little change is noted: the reverse of the petals. gradually lighten to 53B and 53C and the bases and points of attachment blend together and become more yellow in color, to near 11B on the adaxil surface and near 11C on the reverse; the upper surfaces of the petals virtually remain unchanged in color. When the white streak is present, its color remains unchanged even though the color at the base of the petals from where it originates becomes deeper yellow.

Petaloids: Texture: same as petals.

*Color.*—The same as an outer petal in particular those with the white streaks.

*Size.*—Width — 5/32 to 9/32 inch wide at the widest point and ½ to ⅝ inch long.

*Unique characteristics.*—When present, are deformed petals, sometimes with the base appearing to be only ½ of a petal but the outer edge being 80% to 90% of a petal and occasionally being connate with a stamen.

General tonality: Always a deep velvety red.

REPRODUCTIVE ORGANS

Stamens, filaments and anthers:

*Arrangement.*—Regularly arranged around styles.

*Quantity.*—96 to 100.

*Filaments.*—Length — 9/32 to 3/32 inch. General color — translucent, a pale red, near 45C and near 15D, a pale yellow, at the base.

*Anthers.*—Color — near 18C.

*Pollen.*—Color: near 15A. Quantity: ample amount Fertility: fertile.

Pistils, styles and stigmas:

*Quantity.*—About 28.

*Styles.*—(Thin; being undulate and thinnest at point of connection to receptacle. Length: 5/32 inch long becoming 9/32 inch long as flower matures Color — near 185B (lighter red).

*Stigmas.*—Color — near 55D, translucent-appearing, light pink and near 2D, a light celery green, at attachment.

Hips: (There are no hips to observe at the time of the writing of this application. Generalized information supplied here is from notes taken previously.)

*Shape.*—Globular.

*Size.*—11/32 inch diameter.

*Surface texture.*—Smooth. Seeds: viable; may protrude Color — off white Number per hip — only 1 to 3 small seeds per hip.

PLANT

Habit: Upright, well-branched, flowers held above the plant.

Growth: Vigorous, uniformly branched.

*Height.*—16 to 22 inches.

*Width.*—Up to 20 inches.

*Root initiation form cuttings.*—6–10 days.

*Length of internodes.*—When grown in full sun, usually 13/16 inch, alternate.

*Length of flowering stem.*—5 to 8 inches.

Foliage: Pinnately compound with 5 and 7 leaflets, occasionally with 3.

*Size of mature leaf.*—3½ inches from stem to tip when measured along the rachis.

*Leaflets.*—Shape — ovate with an acute apex and oval base. Size mature terminal leaflet — width ⅞ inch at its widest point and up to 1½ inches in length. Color new foliage — anthocyanin coloration — weak upper surface, dark green, near 137A under surface, a lighter yellow-green, near 146D Color older foliage — anthocyanin coloring absent upper surface, an even darker green, near 139A under surface, near 191A, a softer green from the greyed-green group Appearance — upper surface, semi-glossy; underside, matte with main vein protruding and other veins are clearly visible Texture — upper surface is glabrous, under surface — leathery Surface — from 0 to 3 single hairs randomly on either or both leaf surfaces Edge — near even serration with a gland only on the tip of each serrate.

*Petiole/rachis.*—Color on young leaf — upper side is near 147C in the groove and the ridges are near 187D. underside is between 147C and 147D.

*Color on old leaf.*—Upper side along the ridges, the same as the upper leaf surface, a very dark green, near 139A, and a lighter yellow-green, near146D, in the groove underside is yellow-green, near 144A. Rachis: size — from ¾ inch long, usually on 5-leaflet leaf, to 1 inch long, usually on 7-leaflet leaf and a 3/64 inch diameter Texture — usually only one stipate gland along the ridges and hairs in the groove where the leaflets are attached to the rachis, underside may have a few hairs.

*Petiole.*—½ to 1 inch long, most often 9/16 to 11/16 inch long and about 1/16-inch diameter. Texture — usually 3 to 5 stipate glands along the ridges, underside may have a few hairs.

Petiolule: (Occasionally may be non-existent except to terminal leaflet) usually the coloring is the same as that part of the rachis to which it is attached.

*Surface.*—All surfaces of the petiolule to the basil leaflet are the same as those on the rachis; all surfaces of the other petiolules are glabrous.

*Size.*—1/32 inch diameter; 3/8 to 1/2 inch long to terminal leaflet and up to 3/64 inch long to other leaflets but varying down to non-existent.

Stipules: 2 at the base of each leaf are often nearly an identical pair; occasionally one or both appearing non-existent to the naked eye, either entirely or just that portion attached to the petiole; appearing to be extensions of the ridges along the petiole and may continue in an upward direction (adaxil) or may be parallel to the petiole; regardless of the position or appearance of the attached portion of the stipules, the detached extensions may be parallel to the petiole, incline adaxial, decline adaxial and paired extensions may differ from each other in position. Margins are unevenly and irregularly serrated with each serrate terminating with a gland.

*Edges.*—Do not roll back.

*Size.*—On mature leaf usually measuring 1/4 inch in length, attached for 3/16 inch, then angling out at a 40° to 50°-angle form the petiole; paired stipules are most often very near the same length, usually not varying by more than 1/64 inch.

*Width.*—Up to 3/32 inch and down to appearing non-existent, paired stipules are usually not the same width. Surface — glabrous; veins obvious from abaxil surface.

*Other foliar appendages.*—At the base of each peduncle there usually is a pair of lanceolate, foliar appendages with truncate bases and acuminate apices, anywhere from 11/32 to 1 inch long and/32 to 8/32 inch wide at the widest part; occasionally a foliar appendage will terminate in a blobbed leaf, usually longer than the appendage it is attached to; the foliar appendages have the same color, margins and surface appearance as the sepals; bi-lobed leaves, when present have the same indicant as the leaflets except for a more pronounced serrated edge; occasionally there are also adventitious leaves, below the peduncle and before the first true pinnate leaves, which are often bi-lobbed and attached to the flowering stem by sepalous appendages and being 1½ inch or more from point of attachment to the stem to the apex.

Resistance: Very good resistance to black spot, downey mildews and to insects, moderately susceptible to powdery mildew, no rust observed.

Wood: New growth often originates from the roots, below ground level, creating numerous stalks of similar size, the oldest stalks are often of a smaller diameter as they originated when the plant was very young so they are often equal to or slightly smaller than the primary laterals.

*New wood.*—Texture — nearly glabrous with only a very few single hairs. Color — near 147A. Appearance — there are numerous stomata the entire length of every stem surface, which are clearly visible under an ×3 microscope, occasionally in vertical rows or circular patterns but most often randomly located.

*Old wood.*—Texture glabrous. Color — near 147B.

*Diameter.*—Mature main stalks, 3/8 inch, primary laterals, 3/16 inch; flowering stems 10/64 inch near attachment to lateral decreasing to 7/64 inch right below the peduncle.

*Appearance.*—The areas of cork cambium, a light brown between 177C and 197B, appear along the stomata usually after the 5th or 6th year and do not completely cover the old wood; lenticels are contiguous and clearly visible at ×3 or stronger and are too numerous to counted by the average person.

Prickles: Quantity on main stalks is none to 4 per inch, on laterals — 3 to 5 per inch.

*Length.*—7/64 to 11/64 inch in length, young or old.

*Form.*—Obovate-acuminate where it attaches to the stem, angled slightly downward, tapering quickly to a point, upper profile being straight, lower profile being slightly curved.

*Color.*—When young, is near 183C when old — near 177D.

Hardiness: Tested hardy in zones 4 through 9, with winter protection recommended for zones 6 and colder. Plants held up very well under testing in American Horticultural Society heat zones 9 through 1.

What is claimed is:

1. A new and distinct variety of hardy, miniature rose plant is claimed, substantially as illustrated and described, with long lasting flowers of a dark red tonality and exhibition, hybrid-tea form, on a vigorous and upright plant with dark green, semi-glossy foliage, having overall good disease resistance and suitable for production from softwood cuttings in pots.

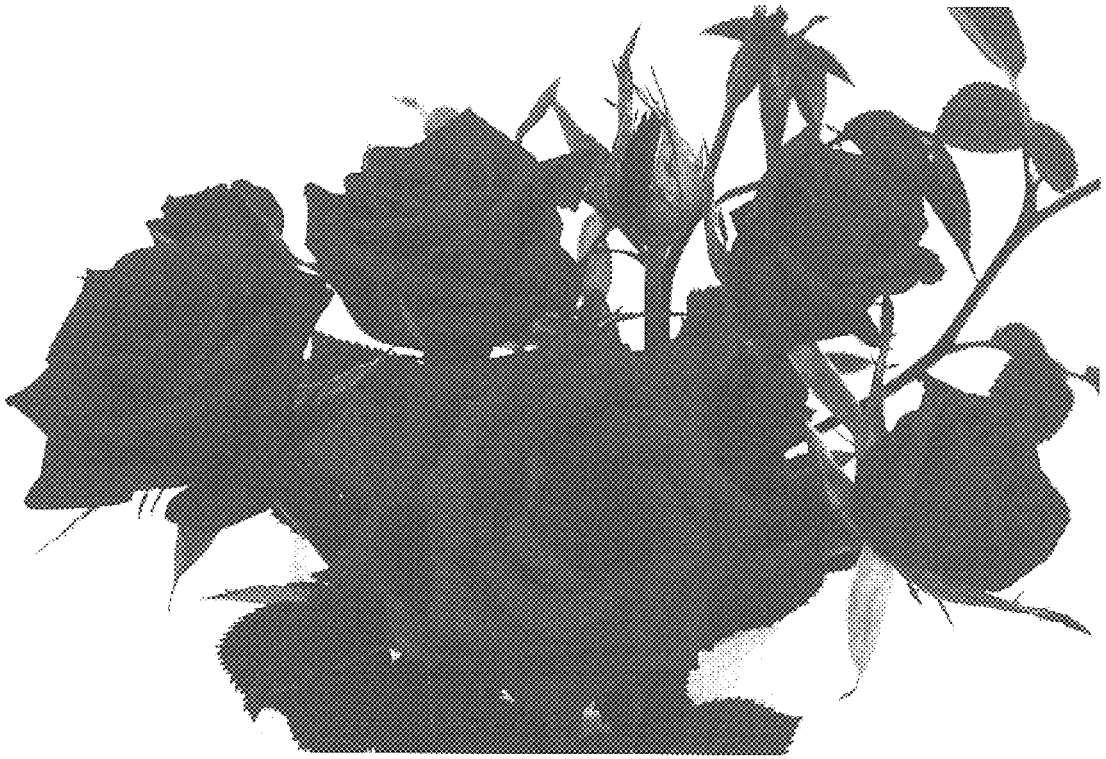

* * * * *